United States Patent [19]
Giolito et al.

[11] 3,931,366
[45] Jan. 6, 1976

[54] COLOR IMPROVEMENT OF PHOSPHATE ESTERS

[75] Inventors: Silvio L. Giolito, Whitestone, N.Y.; Don Keith Worster, Point Pleasant, W. Va.

[73] Assignee: Stauffer Chemical Company, Westport, Conn.

[22] Filed: Dec. 23, 1974

[21] Appl. No.: 535,888

[52] U.S. Cl. .................................. 260/975; 260/989
[51] Int. Cl.$^2$ ............................................ C07F 9/12
[58] Field of Search ............................ 260/989, 975

[56] References Cited
UNITED STATES PATENTS

| | | | |
|---|---|---|---|
| 3,356,775 | 12/1967 | Mitchell | 260/989 X |
| 3,576,923 | 4/1971 | Randell et al. | 260/966 |
| 3,681,482 | 8/1972 | Patel et al. | 260/989 |
| 3,706,823 | 12/1972 | Rampy et al. | 260/975 X |

*Primary Examiner*—Richard L. Raymond
*Attorney, Agent, or Firm*—Charles B. Rodman

[57] ABSTRACT

A method for decolorizing and stabilizing alkylphenyl esters of phosphoric acid which comprises the in situ addition of an effective amount of $PCl_3$ to the $POCL_3$ reacted with an alkyl phenol so as to produce a decolorized and stabilized phosphate ester.

7 Claims, No Drawings

COLOR IMPROVEMENT OF PHOSPHATE ESTERS

BACKGROUND OF THE INVENTION

This invention relates to the decolorization and stabilization of alkylphenyl esters of phosphoric acid. The production of low color and color stable phosphate esters from alkylphenol precursors has been a long recognized problem. In the conventional production of phosphate esters from alkylphenols, undesirable color formation frequently occur. Color can decrease the phosphate ester's value as a commercial product.

Alkylphenyl esters of phosphoric acid find extensive use as plasticizers for nitrocellulose and polyvinyl chloride (PVC) compositions. In addition, they also serve as additives for gasoline, functional fluids, oils, and are useful as flame retardants in plastics, and the like.

The preparation of alkylphenyl esters of phosphoric acid is generally accomplished by the addition of phosphorus oxychloride, ($POCl_3$) to selected phenols, such as cresols, xylenols, and the like, and gradually heating the resulting reaction mixture to about 180°C. The reaction is accelerated by the presence of a Friedel-Crafts catalyst such as aluminum chloride, ($AlCl_3$). In conventional processing, the reaction product is vacuum distilled to remove unreacted phenols as an initial fraction, and the alkyl-phenyl phosphate ester as a product fraction, leaving high boiling point materials and the catalyst in the residue. The distilled product fraction is then washed thoroughly with sodium hydroxide solution to remove free phenol and acidic materials, followed by water washing. The product fraction is then generally treated with activated carbon to remove color causing impurities.

This process, which works very well with esters produced from conventional by-product alkylphenols, produces unsatisfactory material when applied to mixed alkylphenols produced by the alkylation of phenol with olefins. It is found that the products discolor upon exposure to air, exposure to heat, or storage in the dark. The discoloration has been attributed to the presence of di(o-alkyl) phenols in the alkylated phenol. Steric hindrance caused by the double ortho substitution in 2,6 dialkylphenols and in 2,4,6-trialkylphenols renders the phenols unresponsive to washing with sodium hydroxide solution, so that they are not removed by the caustic wash.

These so-called "hindered phenols," can oxidize in the presence of air to form highly colored quinones, which are the source of undesirable discoloration in the product. These quinones can bleach somewhat in the light, however, color will reappear upon storage in the dark. The color can intensify when the ester is mixed or milled with polyvinyl chloride (PVC) under the influence of air and heat.

Thus, for example, in the case of 2,6-diisopropylphenol, the corresponding diphenoquinone or benzoquinone is highly colored. Esters made from mixtures of alkylated phenols which contain di-orthoalkylphenols such as 2,6-diisopropylphenol can be too highly colored for many uses, particularly for use as plasticizers. High color phosphate esters have limited utility for plasticizer use and are less marketable.

Color formation in phosphate esters is discussed in U.S. Pat. No. 3,681,482, which correlates the degree of color formation in phosphate esters to the degree of alkyl substitution of the aryl ring. Accordingly, tris(methylphenyl) phosphate will produce less color than tris(dimethylphenyl) phosphate. This may be explained by the fact that the tris(methylphenyl) phosphate has only one methyl group substituted on the aryl ring, whereas tris(dimethylphenyl) phosphate has two methyl groups substituted on the aryl ring and, therefore, has more color.

A number of proposals have been made for methods to overcome the problem of undesirable color formation. For example, U.S. Pat. No. 1,958,210 discloses the use of activated carbon to decolorize and remove oxidizable impurities from phosphate esters. This approach is unsatisfactory because activated carbon is not an effective decolorizing agent for alkylphenyl phosphate esters. In certain instances, for example, in the decolorization of isopropylphenyl diphenyl phosphate ester, the use of activated carbon may increase color formation.

U.S. Pat. No. 2,113,951 discloses a method wherein an alkylphenol such as cresylic acid is distilled in the presence of a mineral acid such as sulfuric, hydrochloric or phosphoric acid, to purify it. The purified cresylic acid is then employed in the manufacture of tricresyl phosphate esters which are supposed to be more stable to the action of heat and light than the corresponding ester made from alkylphenols distilled in the absence of an inorganic acid. The disadvantage of this process is that the phenolic residues oxidize to colored quinones, and must be thoroughly distilled in order to remove them and avoid further color formation.

Another method for reducing color is proposed in U.S. Pat. No. 3,681,482 wherein sodium borohydride is used to permanently bleach and color stabilize tris (alkylphenyl) phosphate esters containing 2,6-diisopropylphenol and the corresponding diphenoquinone. The sodium borohydride reduces the diphenoquinone to The colorless 2,6-diisopropylphenol which, however, remains in the product and is a potential source of discoloration if the product is exposed to oxidizing conditions. Sodium borohydride treatment is also expensive in cost of materials and time, as several hours to overnight treating times are necessary.

Thus, it can be seen that the methods proposed in the prior art, are not commercially effective for removing color from alkylphenol esters of phosphoric acid, or do not improve the PVC mill stability when these esters are used as PVC plasticizers.

SUMMARY OF THE INVENTION

In accordance with the present invention, a method for removing color from alkylphenyl esters of phosphoric acid which also improves the mill stability of these esters when they are used as plasticizers for PVC has now been discovered.

The method comprises the use of small amounts of $PCl_3$ in the $POCl_3$ used in the phosphorylation of alkaryl phenols. The phosphate esters prepared in this manner are decolorized and stabilized against subsequent color formation. This method produces a low color, stable phosphate ester.

DETAILED DESCRIPTION OF THE INVENTION AND THE PREFERRED EMBODIMENTS

Permanent removal of color from colored phosphate esters according to the method of this invention is achieved by the in situ addition of an effective amount of $PCl_3$ to the $POCl_3$ used in the phosphorylation of alkylated phenol mixtures. It has been found that the addition of the $PCl_3$ to the $POCl_3$ used in the phosphorylation reaction produces a decolorized phosphate ester which is stabilized against subsequent color formation.

This invention is applicable to all phosphate esters which are made from alkylated phenol mixtures which contain hindered phenols, e.g., phenols containing alkyl groups on both positions ortho to the hydroxyl group. The esters may contain 0.5 to 3 alkylaryl groups and 0 to 2.5 phenyl groups. Preferably, the triaryl phosphate esters treated by the process of this invention are a mixture of esters containing 1 to 2 alkaryl groups. The esters correspond to the general formula:

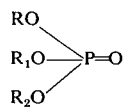

Where R is alkaryl and $R_1$ and $R_2$ may be alkyl, alkaryl, aralkyl or aryl, and wherein the alkyl groups can contain from 1 to 20 carbon atoms and more preferably, from 1 to 12 carbon atoms. Som triphenylphosphate may also be present.

The alkylated phenols which contain hindered phenols are usually made by alkylating phenol with $C_2-C_{r2}$ unsaturated hydrocarbons such as ethylene, propylene, isobutylene and its isomers, amylene and its isomers, tripropylene, tetrapropylene, decene, dodecene, diisobutylene and the like.

Typical examples of alkyl radicals are as follows: methyl, ethyl, normal propyl, isopropyl, normal butyl, isobutyl, secondary butyl, tertiary butyl, normal amyl, isoamyl, 2-methylbutyl, 2,2-dimethyl propyl, 1-methyl butyl, diethylmethyl, 1,2-dimethyl propyl, tertiary amyl, normal hexyl, 1-methylamyl, 1-ethyl butyl, 1,2,2,-trimethyl propyl, 3,3-dimethyl butyl, 1,1,2-trimethyl propyl, 2-methyl amyl, 1,1-dimethyl butyl, 1-ethyl 2-methyl propyl, 1,3-dimethyl butyl, isohexyl, 3-methylamyl, 1,2-dimethyl butyl, 1-methyl 1-ethyl propyl, 2-ethyl normal heptyl, 1,1,2,3-tetramethyl propyl, 1,2-dimethyl 1-ethyl propyl, 1,1,2-trimethyl butyl, 1-isopropyl 2-methyl propyl, 1-methyl 2-ethyl butyl, 1,1-diethyl propyl, 2-methyl hexyl, 1,1-dimethyl amyl, 1-isopropyl butyl, 1-ethyl 3-methyl butyl, 1,4-dimethyl amyl, isoheptyl, 1-methyl 1-ethyl butyl, 1-ethyl 2-methyl butyl, 1-methyl hexyl, 1-propyl butyl, normal octyl, 1-methyl heptyl, 1,1-diethyl 2-methyl propyl, 1,1,3,3-tetramethyl butyl, 1,1-diethyl butyl, 1,1-dimethyl hexyl, -methyl 1-ethyl amyl, 1-methyl 1-propyl butyl, 2-ethyl nexyl, 6-methyl heptyl, normal nonyl, 1-methyl octyl, 1-ethyl heptyl, 1,1-dimethyl heptyl, 1-ethyl 1-propyl butyl, 1,1-diethyl 3-methyl butyl, diisobutyl methyl, 3,5,5-trimethyl hexyl, 3,5-dimethyl heptyl, normal decyl, 1-propyl heptyl, 1,1-diethyl hexyl, 1,1-dipropyl butyl, 2isopropyl 5-methyl hexyl and $C_{11}-C_{20}$ alkyl groups.

Also included are aralkyl groups, e.g., benyzyl, alpha- or beta-phenylethyl, alpha,alpha dimethylbenzyl and the like. Also included are cyclohexyl, cycloheptyl, cyclododecyl and the like. Typical examples of aryl and alkaryl radicals are phenyl, cresyl, xylyl, alkoxylated phenyl, isopropylphenyl, butylphenyl, alpha-alkylbenzylphenyl and alpha, alpha-dialkylbenzylphenyl, e.g., alpha-methylbenzylphenyl, alpha, alpha dimethylbenzyl phenyl, tert-nonylphenyl, amylphenyl, tert-butylphenyl, isooctylphenyl, dodecylphenyl, tertiary octylphenyl and the like.

The invention is hereinafter exemplified by first showing the preparation of an ester via the alkylation of phenol with an olefin, followed by addition of $POCl_3$. These alkylated phenols produce esters which are similar to those produced with conventional by-product coal tar cresylic acids or methylphenols.

The esters are generally made by reacting an alkylphenol with $POCl_3$ in the presence of a Friedel-Crafts catalyst at an elevated temperataure, typically about 180°C., until the reaction is complete, as noted by the cessation of HCl evolution. The reaction mixture is then heated to distill excess phenols overhead. The temperature and/or vacuum is then increased and the phosphate ester product is distilled leaving the catalyst and a small amount of high boiling distillation residue.

Conventionally, the ester product is washed with aqueous alkali to remove free phenols which are generally present in the range of about a few tenths of a percent. The washed product is separated from the water and generally treated with activated carbon and a filter aid, such as diatomaceous earth, and filtered. However, product discoloration caused by hindered phenols in the presence of air and heat can ensue, rendering the product unsuitable for use in the applications where lack of color is important.

In accordance with this invention an effective amount of $PCl_3$ is contacted with the $POCl_3$ at ambient temperature. The mixture is then contacted with isopropyl phenol at ambient temperature. A catalyst, such as, $AlCl_3$ is then added, and the charge is heated gradually from about 80°C. to 180°C. for several hours.

The amount of $PCL_3$ may vary in amount from about 0.1% to about 10% by weight of $POCl_3$. Larger quantities of the $PCl_3$ can be employed, but no advantage is accrued thereby. It is preferred to use an amount ranging from about 0.5% to about 8% by weight of the $POCl_3$, with about 2% to about 6% being particularly preferred. The particular amount of $PCl_3$ employed in any given instance will to some extent be influenced by a number of factors which include the extent of color improvement desired, particular phosphate ester produced, treatment time, and the like.

The method of this invention is generally conducted under atmospheric pressure. However, higher or lower pressures may be used. It may also be conducted under an inert atmosphere, such as nitrogen which serves to repress re-oxidation. The method of this invention may be carried out batch wise or in a continuous manner.

One particular advantage of the invention is that the production of decolorized and stabilized phosphate esters is accomplished without the necessity of additional steps or special treatment.

The following examples are illustrative of the method disclosed above, and provided without any intention that the invention be limited thereto. In the examples and throughout the specification, all parts and percentages are by weight, unless otherwise noted.

EXAMPLE I

A mixture of 7 grams of $PCl_3$ (0.05 mole) and 167.8 grams of $POCl_3$ (1.09 mole) was added to 276 grams (2.0 mole) of isopropyl phenol and 129.6 grams of phenol (1.38 mole) containing 1 gram of anhydrous magnesium chloride catalyst. The charge was placed under a slight nitrogen bleed system and heated from 80°C. to 180°C. for several hours until the evolution of HCl stopped. Weight of the crude ester was 450 grams.

The ester was vacuum distilled through a 6 × 1 column packed with glass spheres to give 405 grams of distillate with a boiling pt. of 198°–245°C/23 mm Hg, and 36 grams of a low boiling fraction having a boiling point of 95°–150°C./24 mm Hg.

The distillate was caustic washed at 70°C. using a low 1.0% caustic solution. It was then water washed at 70°C until a neutral PH of 7 was reached. The washed ester was dried by vacuum stripping at 80°C/5 mm Hg. to give a product having the following properties:

> Acid Number = 0.10
> $n_D^{25}$ = 1.5493
> $d_{25}$ = 1.13
> SUS/100 F. = 125
> APHA color value = 25
> $P^{+3}$ = 0.304%

The ester was placed in the dark for one week, during which the APHA color value remained at 25.

EXAMPLE II

The run of Example I was repeated using the same concentration of reagents to give a finished ester having the following properties:

> Acid No. = 0.10
> $n_D^{25}$ = 1.5490
> $d_{25}$ = 1.14
> APHA = 25
> $p^{+3}$ = 0.33%

The ester remained color stable after one week in the dark.

What is claimed is:

1. In a method for producing alkylphenyl esters of phosphoric acid which comprises the alkylation of phenol with an olefin followed by the addition of $POCl_3$ in the presence of a Friedel-Crafts catalyst at an elevated temperature, the improvement which comprises the in situ contacting of an effective amount of $PCl_3$ with the alkylation mixture, to produce an ester which is decolorized and stabilized against subsequent color formation.

2. The method of claim 1 wherein said alkylphenyl esters correspond to the formula:

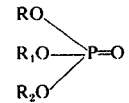

where R is alkaryl and $R_1$ and $R_2$ are selected from the group consisting of alkyl, aralkyl, alkaryl and aryl, and wherein the alkyl groups contain from 1 to about 20 carbon atoms.

3. The method of claim 2 wherein the alkyl groups contain from 1 to about 12 carbon atoms.

4. The method of claim 1 wherein the alkylphenyl esters contain unreacted phenols.

5. The method of claim 1 wherein the alkyl phenyl ester of phosphoric acid is an ispropyl phenyl phenylphosphate.

6. The method of claim 1 wherein the $PCl_3$ contacting is conducted under an inert atmosphere.

7. The method of claim 6 wherein said inert atmosphere comprises nitrogen.

* * * * *

UNITED STATES PATENT AND TRADEMARK OFFICE
CERTIFICATE OF CORRECTION

PATENT NO. : 3,931,366
DATED : January 6, 1976
INVENTOR(S) : Silvio L. Giolito and Don Worster It is certified that error appears in the above—identified patent and that said Letters Patent are hereby corrected as shown below:

Column 3, line 23 "Som" should read --Some-- ;
Column 3, line 26 "$C_2-C_{r2}$" should read --$C_2-C_{12}$-- ;
Column 5, line 1 "6 x 1" should read
-- 6 by 1 inch --.

Signed and Sealed this

Fourteenth Day of December 1976

[SEAL]

Attest:

RUTH C. MASON
Attesting Officer

C. MARSHALL DANN
Commissioner of Patents and Trademarks